United States Patent [19]

Moorehead

[11] Patent Number: 4,639,530
[45] Date of Patent: * Jan. 27, 1987

[54] PROCESS FOR MAKING MALEIC ANHYDRIDE

[75] Inventor: Eric L. Moorehead, Diamond Bar, Calif.

[73] Assignee: Union Oil Company of California, Los Angeles, Calif.

[*] Notice: The portion of the term of this patent subsequent to Nov. 6, 2001 has been disclaimed.

[21] Appl. No.: 749,556

[22] Filed: Jun. 27, 1985

Related U.S. Application Data

[60] Division of Ser. No. 666,997, Oct. 31, 1984, Pat. No. 4,604,371, which is a continuation-in-part of Ser. No. 461,942, Jan. 28, 1983, Pat. No. 4,481,363, Ser. No. 646,291, Aug. 29, 1984, abandoned, Ser. No. 492,163, May 6, 1983, Pat. No. 4,562,291, and Ser. No. 492,226, May 6, 1983, said Ser. No. 461,942, is a division of Ser. No. 289,806, Aug. 3, 1981, Pat. No. 4,388,221, said Ser. No. 646,291, is a continuation-in-part of Ser. No. 461,942, which is a division of Ser. No. 289,806, said Ser. No. 492,163, and Ser. No. 492,226, each is a continuation-in-part of Ser. No. 275,370, Jun. 19, 1981, abandoned.

[51] Int. Cl.$^4$ .......................................... C07D 307/60
[52] U.S. Cl. ..................................... 549/260; 549/259
[58] Field of Search ................................ 549/259, 260

[56] References Cited

U.S. PATENT DOCUMENTS 3,156,705 11/1964 Kerr ............................ 549/260
3,243,385 3/1966 Sennewald et al. .......... 260/465.3
3,288,721 11/1966 Kerr ............................ 502/209
3,370,081 2/1968 Sennewald et al. .......... 502/209
3,506,400 4/1970 Eberly, Jr. et al. ............ 502/78
3,640,681 2/1972 Pickert ........................ 502/78
3,700,749 10/1972 Robinson et al. ............. 502/78
3,702,886 11/1972 Argauer et al. .............. 208/111
3,751,502 8/1973 Hayes et al. ................. 585/401
3,775,508 11/1973 Pitzer ......................... 585/654
3,789,078 1/1974 Nolan et al. ................ 260/680 E
3,856,881 12/1974 Manning ..................... 585/629
3,862,146 1/1975 Boghosian ................... 549/260
3,867,411 2/1975 Raffelson et al. ............ 549/260
3,884,835 5/1975 Vaughan ..................... 252/1
3,888,886 6/1975 Young et al. ................. 549/260
3,890,218 6/1975 Morrison ..................... 208/135
3,914,332 10/1975 Dickason ..................... 549/260
3,915,892 10/1975 Harrison ..................... 502/209
3,925,447 12/1975 Gelbein ....................... 260/465 C
3,927,138 12/1975 Walker ........................ 558/661
3,931,046 1/1976 Weinstein et al. ............ 502/209
3,972,832 8/1976 Butter et al. ................ 502/77
3,977,998 8/1976 Freerks et al. .............. 502/209
4,061,724 12/1977 Grose et al. ................ 423/335
4,062,873 12/1977 Harrison ..................... 549/259
4,064,070 12/1977 Harrison ..................... 502/209
4,073,865 2/1978 Flanigen et al. ............. 423/339
4,092,269 5/1978 Mount et al. ................ 502/209
4,104,294 8/1978 Grose et al. ................ 556/173
4,123,388 10/1978 Kerr et al. .................. 502/209
4,151,116 4/1979 McDermott .................. 549/260

4,153,577 5/1979 Barone ........................ 502/209
4,165,299 8/1979 Pedersen ..................... 549/259
4,165,300 8/1979 Dolhyj et al. ............... 502/304
4,171,316 10/1979 Pedersen ..................... 549/259
4,179,404 12/1979 Barone ........................ 502/209
4,206,084 6/1980 Strojny et al. .............. 502/242
4,244,879 1/1981 Bremer et al. .............. 549/259
4,246,141 1/1981 Hass et al. .................. 502/78
4,246,421 1/1981 Bartek et al. ............... 546/352
4,247,419 1/1981 Vartuli et al. .............. 502/209
4,252,680 2/1981 Walker et al. .............. 502/308
4,270,017 5/1981 Young ......................... 585/437
4,283,306 8/1981 Herkes ........................ 502/202
4,292,201 9/1981 Vartuli et al. .............. 502/209
4,292,202 9/1981 Vartuli et al. .............. 502/209
4,309,275 1/1982 Mulaskey .................... 208/109
4,309,276 1/1982 Miller ........................ 208/109
4,311,611 1/1982 Sasaki et al. ............... 502/22
4,314,983 2/1982 Hass et al. .................. 423/542
4,333,853 6/1982 Milberger et al. .......... 502/209
4,347,395 8/1982 Chu et al. ................... 585/420
4,360,453 11/1982 Lemanski et al. ........... 502/209
4,361,501 11/1982 Blum et al. ................. 502/209
4,362,653 12/1982 Robinson ..................... 502/242
4,370,490 1/1983 Gruber et al. .............. 560/214
4,371,457 2/1983 Chu ............................ 502/77
4,377,502 3/1983 Klotz ......................... 502/77
4,388,221 6/1983 Moorehead .................. 502/209
4,394,300 7/1983 Chu et al. ................... 502/77
4,396,536 8/1983 Bremer et al. .............. 502/208
4,428,862 1/1984 Ward et al. ................. 502/77
4,454,245 6/1984 Robinson et al. ........... 521/136
4,454,342 6/1984 Gaffney et al. ............. 560/204
4,455,388 6/1984 Robinson et al. ........... 502/209
4,481,363 11/1984 Moorehead .................. 549/260
4,562,269 12/1985 Moorehead .................. 549/259

FOREIGN PATENT DOCUMENTS 81200173.3 2/1981 European Pat. Off. .

OTHER PUBLICATIONS

"When is a Zeolite Not a Zeolite?", by Lovat V. C. Rees, Nature, vol. 296, pp. 491–492, Apr. 8, 1982.
"Silicalite—2, A Silica Analogure of the Aluminosilicate Zeolite ZSM—11", by D. M. Bibby et al., Nature, vol. 280, pp. 664–665, Aug. 23, 1979.
"Silicalite, A New Hydrophobic Crystalline Silica Molecular Sieve", by E. M. Flanigen et al., Nature, vol. 271, pp. 512–516, Feb. 9, 1978.

(List continued on next page.)

[57] ABSTRACT

An oxidation catalyst of large surface area for converting $C_4$ to $C_{10}$ hydrocarbons to maleic anhydride comprises the oxides of vanadium, phosphorus and, optionally and preferably, tin, in combination with a microporous crystalline silica or a crystalline zeolite having a silica-to-alumina ratio of at least 6.0.

34 Claims, No Drawings

OTHER PUBLICATIONS

"Chemical and Physical Properties of the ZSM—5 Substitutional Series", by D. H. Olson et al., *Journal of Catalysis*, vol. 61, pp. 390–396, (1980).

"Silicates", by Cotton and Wilkinson, *Advanced Inorganic Chemistry*, 2nd ed., 1966, pp. 469–474.

"The Structure and the Activity of Vanadyl Phosphate Catalysts", by Michihiro Nakamura et al., *Journal of Catalysis*, vol. 34, pp. 345–355, (1974).

"Reactions on ZSM—5 Type Zeolite Catalyst", by J. R. Anderson et al., *Journal of Catalysis*, vol. 58, pp. 114–130, (1979).

"Pentasil Family of High Silica Crystalline Materials", by G. T. Kokotailo et al., in *The Properties and Applications of Zeolites*, ed. R. P. Tounsend, the Proceedings of a Conference organized jointly by the Inorganic Chemicals Group of the Chemical Society and The Society of Chemical Industry (Burlington House, London), Apr. 18–20, 1979, pp. 133–139.

"Resolving Crystallographically Distinct Tetrahedral Sites in Silicalite and ZSM—5 by Solid—State NMR", by C. A. Fyfe et al., *Nature*, vol. 296, Apr. 8, 1982, pp. 530–533.

"Research Article Triggers Dispute on Zeolite", by Budiansky, *Nature*, vol. 300, Nov. 1982, p. 309.

"Zoned Aluminum Distribution in Synthetic Zeolite ZSM—5", by Ballmoos et al., *Nature*, vol. 289, Feb. 26, 1981, pp. 782–783.

U.S. application Ser. No. 492,163, filed May 6, 1983, Eric L. Moorehead.

U.S. application Ser. No. 492,226, filed May 6, 1983, Eric L. Moorehead.

U.S. application Ser. No. 592,422, filed Mar. 21, 1984, Eric L. Moorehead and Paul R. Robinson.

U.S. application Ser. No. 595,333, filed Mar. 30, 1984, Eric L. Moorehead and Paul R. Robinson.

U.S. application Ser. No. 646,291, filed Aug. 29, 1984, Eric L. Moorehead.

U.S. application Ser. No. 666,997, filed Oct. 31, 1984, Eric L. Moorehead.

U.S. application Ser. No. 667,000, filed Oct. 31, 1984, Paul R. Robinson and Eric L. Moorehead.

U.S. application Ser. No. 749,557, filed Jun. 27, 1985, Paul R. Robinson and Eric L. Moorehead.

*Primary Examiner*—Henry R. Jiles
*Assistant Examiner*—Bernard I. Dentz
*Attorney, Agent, or Firm*—Dean Sandford; Gregory F. Wirzbicki; Robert A. Franks

PROCESS FOR MAKING MALEIC ANHYDRIDE

CROSS-REFERENCE TO RELATED APPLICATIONS

This application is a division of Ser. No. 666,997, filed Oct. 31, 1984, now U.S. Pat. No. 4,604,371, which is a continuation-in-part of U.S. patent application Ser. No. 461,942 filed Jan. 28, 1983, now U.S. Pat. No. 4,481,363, which is itself a divisional of U.S. patent application Ser. No. 289,806 filed Aug. 3, 1981, now U.S. Pat. No. 4,388,221. Ser. No. 666,997 is also a continuation-in-part of U.S. patent application Ser. No. 646,291, filed Aug. 29, 1985, abandoned which itself is a continuation-in-part of the aforesaid application Ser. No. 461,942, now U.S. Pat. No. 4,481,363, which is a divisional application of the foresaid Ser. No. 289,806, now U.S. Pat. No. 4,388,221. Ser. No. 666,997 is also a continuation-in-part of U.S. patent application Ser. No. 492,163, filed May 6, 1983, now U.S. Pat. No. 4,562,269 and a continuation-in-part of U.S. patent application Ser. No. 492,226, filed May 6, 1983, both of which applications are continuation-in-part applications of U.S. patent application Ser. No. 275,370, filed June 19, 1981, abandoned.

BACKGROUND OF THE INVENTION

The present invention relates to oxidation catalysts, and more particularly to oxidation catalysts for producing maleic anhydride from $C_4$ to $C_{10}$ hydrocarbons.

Essentially all of the catalysts and methods disclosed in the prior art for producing maleic anhydride from $C_4$ and higher hydrocarbons employ oxidation catalysts containing vanadium in a valence state of less than +5. One method of forming such catalysts is to impregnate a catalyst base with a vanadium compound in which the vanadium has a valence of less than +5. Another more desirable method involves impregnating the catalyst with a vanadium compound which has vanadium in the +5 valence state and then reducing the vanadium from the +5 valence state to a valence less than +5.

Several references disclose oxidation catalysts containing vanadium-phosphorus mixed oxide catalysts and methods of preparing the same. For example, U.S. Pat. No. 4,179,404 discloses a process for preparing vanadium-phosphorus containing oxidation catalysts which consists of reducing pentavalent vanadium to a valence of less than +5 with a trivalent phosphorus compound. The phosphorus compound is employed in a concentration of from about 75 to 90 percent of the stoichiometric amount necessary to reduce the vanadium to a valency of from +5 to +4.

U.S. Pat. No. 4,153,577 discloses a catalyst complex useful for the partial oxidation of alkanes to the corresponding anhydrides in a vapor phase reaction. The oxidation catalyst used is a reduced vanadium and phosphorus mixed oxide catalyst containing either transition metals, Group IIA metals or rare earth metals.

Another oxidation catalyst suitable for preparing maleic anhydride from normal $C_4$ hydrocarbons is disclosed in U.S. Pat. No. 4,123,388 which relates to a vanadium, phosphorus, copper mixed oxide complex containing an alkali or alkaline earth metal. In addition, tin is described as a desirable metal for incorporating into the catalyst.

U.S. Pat. No. 4,092,269 relates to vanadium-phosphorus oxidation catalysts wherein at least 20 atom percent of the vanadium is in the tetravalent state. A pore modification agent selected from polymeric materials, cellulosic materials, monosaccharides, etc. is added to the catalyst to provide pore diameters between 0.8 to 10 microns. The catalyst is described as useful for the conversion of aliphatic hydrocarbons to maleic anhydride.

U.S. Pat. No. 3,915,892 discloses a method of preparing a vanadium-phosphorus mixed oxide oxidation catalyst utilizing three bulk phase transitions, wherein the average valence of vanadium is maintained in the range of 4.1 to 4.5 and in addition a partial pressure of oxygen is maintained in contact with the mixed oxides formed.

As a rule, the prior art has avoided the use of crystalline aluminosilica zeolites as support materials in catalysts for the production of maleic anhydride. U.S. Pat. Nos. 3,888,886 and 4,165,299, however, vaguely mention "zeolite" and "aluminosilicates," respectively, as possible choices among many catalytic carrier materials for the oxidation of butane to maleic anhydride. But these teachings offer nothing to suggest how a crystalline aluminosilicate zeolite can be employed without the adverse effects so often encountered with their use in the prior art. Indeed, it is not even certain if the teachings in the aforementioned patents specifically refer to crystalline aluminosilicate zeolites.

Accordingly, it is an object of the invention to provide zeolitic catalysts, and methods for their preparation and use, which are useful for the oxidation of $C_4$ to $C_{10}$ hydrocarbons to maleic anhydride.

It is yet another object to provide catalysts for the production of maleic anhydride which have a relatively high surface area and comprise vanadium and phosphorus components supported on a carrier containing a crystalline aluminosilicate zeolite.

It is yet a further object of the invention to provide catalysts for producing maleic anhydride comprising vanadium and phosphorus and a microporous crystalline silica, such as silicalite.

It is yet a further object to provide a method for producing such catalysts, with the vanadium having an average valence in the range of +3.50 to +4.95.

These and other objects of the invention will become more apparent in view of the following specification and claims.

SUMMARY OF THE INVENTION

The present invention is founded on the discovery that catalysts containing vanadium and phosphorus components are useful in combination with carriers containing one or more microporous crystalline silicas and/or one or more crystalline zeolites having a silica-to-alumina ratio ($SiO_2:Al_2O_3$) of at least 6.0. The present invention, therefore, provides a catalyst for producing maleic anhydride wherein the catalyst comprises the elements and/or compounds of vanadium, phosphorus, and, optionally and preferably, tin on a support material comprising a crystalline zeolite having a silica-to-alumina ratio of at least 6.0. The invention further provides a method for producing maleic anhydride by contacting a $C_4$ to $C_{10}$ unsaturated or saturated hydrocarbon with a gas containing molecular oxygen in the vapor phase, under reaction conditions, with a catalyst of the invention.

The invention additionally provides a method of preparing a vanadium, phosphorus, and tin oxidation catalyst which comprises:

(A) forming a catalyst precursor by reacting a vanadium compound and a phosphorus compound in an acidic aqueous solution with a tin compound under reaction conditions which will provide vanadium having an average oxidation state of 3.50 to 4.95;

(B) combining the catalyst precursor with a microporous crystalline silica or a crystalline zeolite having a $SiO_2:Al_2O_3$ of at least 6.0; and (C) calcining the resultant material at an elevated temperature.

DETAILED DESCRIPTION OF THE INVENTION

Catalysts of the present invention comprise the elements and/or compounds, but most preferably the oxides, of vanadium and phosphorus, and optionally and preferably tin, on a support material comprising a microporous crystalline silica or a microporous crystalline aluminosilicate zeolite of silica-to-alumina ratio of at least 6.0, preferably at least 8.0, and most preferably at least 10.0. It is also preferred that the vanadium in the catalyst have an average valence between +4.10 and +4.70, although vanadium in other average valence states, for example, in the range of +3.50 to +4.95, is also useful. In a preferred embodiment, the catalyst contains vanadium, phosphorus, and tin according to the following expression:

$$V_a P_b Sn_c X_d$$

where a is from 0.10 to 1, b is 1, c is from 0.001 to 0.30, and X is one or more anionic species (usually and preferably oxygen) present in an amount which satisfies the valence requirements of the vanadium, phosphorus, and tin. It will be understood by those skilled in the art that the numbers assigned to the subscript letters a, b, and c represent the atomic ratio pertaining to the vanadium, phosphorus, and tin components while the value for d merely satisfies the valence requirements for the particular combination of vanadium, phosphorus, and tin chosen.

Besides vanadium, phosphorus, and tin, other active components may be present in the catalyst of the invention. However, it is highly preferred that the catalyst herein be essentially free of alkali and alkaline earth metals. Addition of alkali and alkaline earth metals tends to make the catalyst active for oxidative-dehydrogenation reactions as opposed to the desired oxidation reaction producing maleic anhydride.

The vanadium components useful as a source of vanadium for the catalyst precursor herein include vanadium itself and many of its compounds, such as ammonium metavanadate and vanadyl sulfate; vanadium oxides, such as vanadium pentoxide; and vanadium oxyhalides, such as vanadium oxytrichloride. Pentavalent vanadium compounds such as ammonium metavanadate and vanadium pentoxide are most highly preferred. However, vanadium in nitrate solutions should be avoided, since nitrates tend to oxidize the vanadium.

The phosphorus components useful as a source of phosphorus in the catalyst of the invention include phosphorus itself as well as the compounds thereof. Normally chosen, however, are phosphorus compounds selected from phosphoric acid, phosphorus pentoxide, ammonium phosphate and diammonium phosphate. The preferred phosphorus compounds are pentavalent phosphorus compounds such as phosphoric acid and phosphorus pentoxide.

It is also highly preferred that a reducing agent be present in the catalyst precursor employed to prepare the catalyst of the invention. It is even more preferable that the reducing agent be selected from reducing agents containing tin, and particularly from divalent tin compounds. Divalent tin compounds preferably employed are selected from stannous chloride, stannous fluoride, stannous bromide, stannous oxide, stannous sulfate, stannous acetate, stannous pyrophosphate, and stannous oxalate. Upon reaction of the tin compound with the vanadium compound, tin +2 (stannous) will be oxidized up to the tin +4 (stannic) oxidation state while vanadium in the 5 oxidation state will be reduced to an average oxidation state less than +5.

The catalyst precursor is preferably produced by dissolving and mixing compounds of vanadium, phosphorus and tin in an alcohol-containing, acidic-aqueous medium such as an ethanol-water mixture further containing hydrochloric acid, hydroiodic acid, hydroformic acid, acetic acid, oxalic acid, maleic acid, citric acid or formic acid. The vanadium-phosphorus-tin compounds are contacted at an atomic ratio of vanadium-phosphorus-tin in the range of 0.10 to 1:1:0.001 to 0.30, usually 0.20 to 1:1:0.002 to 0.20. The atom ratio of vanadium to phosphorus in the starting materials is important since it controls the vanadium to phosphorus atom ratio in the final catalyst. When the oxidation catalysts herein contain a vanadium-phosphorus atom ratio below 0.10 or above 1.0, the yield of maleic anhydride using these catalysts is so low as to render the reaction commercially unattractive. It should be noted that phosphorus aids in stabilizing vanadium in the final catalyst composition, while tin +2 acts as a reducing agent which aids in the reduction of vanadium to a valence state of less than +5. It should additionally be noted that the above-described acids which dissolve the vanadium, phosphorus and tin compounds induce a reaction reducing the vanadium compounds. However, the reduction process takes from one-half hour to about one hour when tin is not present in the reaction medium. Upon the addition of divalent tin to the reaction medium, the reduction of vanadium to a valence of less than +5 takes place almost instantly, i.e., less than one minute. Generally, the vanadium is reduced to an average valence within the range of from +3.50 to +4.95, preferably from +4.10 to +4.70, which preferred range is generally obtained with phosphorus to vanadium ratios of about 2.3:1 to 2.4:1. (The average oxidation state of vanadium is determined herein by the method described by Nakamura et al. in "The Structure and the Activity of Vanadyl Phosphate Catalysts," *Journal of Catalysis*, Volume 34, pages 345 to 355 (1974).)

To prepare the catalyst precursor, conditions are employed to dissolve and react the vanadium, tin, and phosphorus in an aqueous media. Temperatures of from 100° F. to 220° F., especially from 180° F. to 220° F., coupled with a reaction time from ½ hour to 6 hours, normally are sufficient at atmospheric pressure to dissolve and react the vanadium, phosphorus and tin compounds. However, pressures up to 50 p.s.i.g. may be used to shorten the dissolution and reaction times. Generally, agitation effected by mixing, rocking, shaking, stirring, etc., is supplied during the reaction period to ensure complete contact of the reactants.

After the reaction proceeds to completion, the catalyst precursor is concentrated, collected, and preferably mixed with a crystalline zeolite or silica. Particularly preferred are those crystalline silicas and crystalline zeolites which are useful as molecular sieves.

A crystalline zeolite, as defined herein, is a microporous, crystalline substance having cation exchange properties. The preferred zeolites are any of the known natural or synthetic crystalline aluminosilicates having a silica-to-alumina ratio of at least 6.0, preferably at least 8.0, and most preferably at least 10.0, with the kinetic diameter of the pores of the zeolite being at least 5.0 angstroms. The requirement of a silica-to-alumina ratio of at least 6.0 eliminates many well-known zeolites for use herein. For example, zeolite Y is known to vary in silica-to-alumina ratio from 3.0 to 6.0 and even higher. Thus, those forms of Y zeolite of silica-to-alumina ratio greater than 6.0 may be used in the invention, but since most of the common forms of Y zeolite have a silica-to-alumina ratio below 6.0, it can be seen that the requirement herein for a silica-to-alumina ratio of at least 6.0 excludes from the invention most of the Y zeolites presently employed on a commercial basis for cracking, hydrocracking, etc.

Among the many zeolites which may be used in the invention include LZ-210, LZ-211, LZ-10, and LZ-20, all of which are available from Union Carbide. (LZ-210 and LZ-211 are more fully described in European Patent Application Pub. No. 82,211 of Breck et al., herein incorporated by reference in its entirety.) Another useful zeolite is SAPO-5, and others contemplated are zeolites of silica-to-alumina ratio above 6.0 which have been fluorided, preferably by the method disclosed in U.S. Pat. No. 4,297,335, which is herein incorporated by reference in its entirety. Whatever zeolite is employed in the invention, the hydrogen form, imparting acidity to the zeolite, is preferred. Such hydrogen zeolites may be prepared by acid-treating the corresponding sodium zeolite with relatively strong mineral acids, for example hydrochloric acid, nitric acid, etc. Yet other methods for yielding hydrogen zeolites are known in the art.

The most preferred zeolite for use in this invention, i.e., mordenite, is a highly siliceous zeolite generally characterized by a silica-to-alumina mole ratio range of from about 6 to about 20 as found in nature. The mordenite crystal lattice comprises as the basic building block a tetrahedron consisting of one silicon or aluminum atom surrounded by four oxygen atoms. Each tetrahedron belongs to one or more four and five membered rings in the framework. The high degree of thermal stability of mordenite is probably due to the large number of five-membered rings which are energetically favored in terms of stability.

Rings of twelve tetrahedra form pores or channels running parallel along the crystal axis of mordenite to give a tubular configuration. This structure is unique among the aluminosilicates or zeolites, because the channels or tubes do not intersect, and access to the cages or cavities is in one direction only. For this reason mordenite is referred to as two-dimensional. Other, well-known zeolites, for example, faujasite, etc. contain twelve-membered rings of tetrahedra, but they have interconnected cages which allow access from three directions.

Commercially available mordenites range in silica-to-alumina ratio from about 6:1 to as high as 100:1, and even higher silica-to-alumina ratios are possible. Typical synthetic mordenites are prepared by heating an alkali metal aluminate in solution with an alkali metal hydroxide in contact with a silica source such as sodium silicate, reactive amorphous silica gel, or aqueous colloidal silica sol, at a temperature of about 180° to 200° F. Crystallization occurs over a relatively short period of time, for example, eight to twelve hours, and conversion to the hydrogen form is effected by acid-treating.

Synthetic mordenite prepared in accordance with the above described procedure is available commercially from the Norton Company under the tradename of Zeolon. As with the other zeolites for use in the invention, the hydrogen form of mordenite is preferred over the sodium form because the slightly acidic hydrogen mordenite crystal structure enhances the formation of maleic anhydride from $C_4$ to $C_{10}$ hydrocarbons in an oxidation reaction. Also, it is most highly preferred that the mordenite employed in the invention be a large port mordenite, i.e., kinetic diameter of the pores is above about 6.0 angstroms.

Another preferred form of crystalline aluminosilicate zeolite for use herein are the zeolites of the ZSM-5 type, such as ZSM-5, ZSM-11, ZSM-12, ZSM-23, ZSM-35, ZSM-38, and the like, with ZSM-5 being most preferred. ZSM-5 is a known zeolite and is more fully described in U.S. Pat. No. 3,702,886 herein incorporated by reference in its entirety; ZSM-11 is a known zeolite and is more fully described in U.S. Pat. No. 3,709,979, herein incorporated by reference in its entirety; ZSM-12 is a known zeolite and is more fully described in U.S. Pat. No. 3,832,449, herein incorporated by reference in its entirety; ZSM-23 is a known zeolite and is more fully described in U.S. Pat. No. 4,076,842, herein incorporated by reference in its entirety; ZSM-35 is a known zeolite and is more fully described in U.S. Pat. No. 4,016,245, herein incorporated by reference in its entirety; and ZSM-38 is a known zeolite and is more fully described in U.S. Pat. No. 4,046,859, herein incorporated by reference in its entirety. These zeolites are known to readily adsorb benzene and normal paraffins, such as n-hexane, and also certain mono-branched paraffins, such as isopentane, but to have difficulty adsorbing di-branched paraffins, such as 2,2-dimethylbutane, and polyalkylaromatics, such as meta-xylene. These zeolites are also known to have a crystal density not less than 1.6 grams per cubic centimeter, a silica-to-alumina ratio of at least 12, and a constraint index, as defined in U.S. Pat. No. 4,229,282, incorporated by reference herein in its entirety, within the range of 1 to 12. The foregoing zeolites are also known to have an effective pore diameter greater than 5 angstroms and to have pores defined by 10-membered rings of oxygen atoms, as explained in U.S. Pat. No. 4,247,388 herein incorporated by reference in its entirety. Such zeolites are preferably utilized in the acid form, as by replacing at least some of the cations contained in the ion exchange sites of the zeolite with hydrogen ions. This exchange may be accomplished directly with an acid or indirectly by ion exchange with ammonium ions followed by calcination to convert the ammonium ions to hydrogen ions. In either case, it is preferred that the exchange be such that a substantial proportion of the ion exchange sites utilized in the catalyst support be occupied with hydrogen ions.

Also suitable for use in the present invention, in place of the zeolite, or in addition thereto, is a microporous crystalline silica. The preferred form of microporous crystalline silica is silicalite, which is disclosed in fuller detail in U.S. Pat. No. 4,061,724, herein incorporated by reference in its entirety. Another microporous crystalline silica suitable for use is silicalite-2, described in "Silicalite-2, A Silica Analogue of the Aluminosilicate Zeolite ZSM-11," by D. M. Bibby et al., *Nature*, Vol.

280, pp. 64 and 65, Aug. 23, 1979. Methods by which silicalite and other microporous crystalline silicas can be used in vanadium and phosphorus-containing catalysts for producing maleic anhydride are disclosed more fully in my copending U.S. patent applications Ser. Nos. 492,163 and 492,226, both filed May 6, 1983, and both of which are herein incorporated by reference in their entireties.

In addition to providing physical strength and stability to the catalyst, the crystalline zeolite or crystalline silica provides a high surface area upon which the vanadium and phosphorus, and optionally tin, components are deposited. One of the surprising discoveries in the present invention is that the phosphorus-to-vanadium atom ratio required for highly effective oxidation to maleic anhydride is much different for high surface area supports (i.e., those having a surface area of 50 m$^2$/gm or more) than for unsupported catalysts or those supported on low surface area supports (i.e., less than 50 m$^2$/gm). In the latter case, it is usually the case that, to obtain a catalyst having vanadium in an average oxidation state between about 4.1 and 4.7, optimally about 4.5 to 4.6, wherein oxidation reactions are most effective, it is necessary to adjust the phosphorus to vanadium ratio to about 1.2. However, for high surface area supports, it is the discovery of the present invention that higher phosphorus-to-vanadium atom ratios are required, i.e., greater than about 2.0, oftentimes between 2.0 and 2.5, and generally between about 2.2 and 2.4.

It is yet a further discovery of the present invention that the relationship of vanadium average oxidation state and phosphorus-to-vanadium ratio is substantially linear. For example, when the average oxidation state of vanadium in vanadium-phosphorus-tin-silicalite catalysts is plotted as the ordinate (y-axis) of a graph and the phosphorus-to-vanadium ratio is the abscissa (x-axis), a straight line results having a slope of $-0.27$ and intercepting the ordinate (where $x=0$) at a value of 5.14.

To combine the microporous crystalline zeolite or crystalline silica with the vanadium, tin, and phosphorus components, the catalyst precursor previously described may be mixed with the crystalline zeolite or crystalline silica in a proportion such that 50 to 85 percent of the catalyst comprises the crystalline component, and the balance is the catalyst precursor. Optionally and preferably, however, binding agents and additives are added to provide the proper consistency and strength to the final catalyst. The binding agents and additives, when used, usually comprise from 1 to 20, preferably from 3 to 10 weight percent, of the finished catalyst. Suitable binding agents include methyl cellulose, silica, and Catapal TM alumina. Additives suitable for use herein include organic polar solvents such as ethanol, propanol, isopropanol, butanol, etc. The preferred method of mixing the catalyst precursor and zeolite or crystalline silica is by co-mulling. However, other mixing techniques may be used.

The physical form of the catalyst of this invention is not critical. The catalyst may be produced as spheres, pellets, beads, elongated cylinders, and three-lobe or cloverleaf configurations. For example, the composites may be filtered and oven-dried and coarse granules may be obtained by breaking up and sieving the oven-dried cake up to any desired size. Spray-drying the catalyst such that the dried catalyst will pass through a 4 to 200 mesh sieve (U.S.) is another method of producing the desired catalyst. Another method involves extruding the catalyst into a desired configuration using a die to produce the desired shape and thereafter drying the catalyst. A particularly desirable shape is a cylindrical configuration having a diameter of from 1/16 inch to ⅛ inch and a length of from ¼ inch to ½ inch.

The final catalyst is activated by calcination which preferably is performed in an air or oxygen atmosphere at a temperature of from about 400° F. to about 1200° F., for about ¼ hour to about 6 hours, usually from about ½ hour to about 4 hours.

The catalyst thus produced is especially suited for oxidizing $C_4$ to $C_{10}$ hydrocarbons to maleic anhydride and preferably has a surface area greater than 50 M$^2$/gm, for example from 100 M$^2$/g to 450 M$^2$/g, a pore volume of from 0.1 cc/g to 0 8 cc/g and a compacted bulk density of from 0.5 to 1.5. A highly preferred surface area for the catalyst of the invention is from 150 to 400 M$^2$/g.

It is highly preferred, when olefins are the feed to be converted to maleic anhydride, that ZSM-5 or silicalite or other pentasil-type materials be present in the catalyst, whereas if an alkane is the feed of choice, then a mordenite or other large pore zeolite be present in the catalyst. The reason for this is that it has been found that pentasil forms of the present catalyst are more effective when treating olefins while mordenite and other large pore zeolites are more effective when treating alkanes.

In order to carry out the oxidation reactions of the present invention, a wide variety of reactor vessels may be employed. For example, conventional fluidized bed reactor and fixed-bed or tube, heat exchanger-type reactors are satisfactory, the details of the operation of such reactors being well known to those skilled in the art. The oxidation reaction is an exothermic reaction, thus necessitating relatively close control of the reaction temperature. It is desirable to have the surface of the reactor at a constant temperature and some medium may be necessary to conduct heat away from the reactor to aid temperature control. Examples of desirable mediums include water coolant, molten sulfur, mercury, molten lead, or eutectic salt baths, for example a sodium nitrate-sodium nitrite-potassium nitrate eutectic constant temperature mixture. An additional method of temperature control is to use a metal block reactor whereby the metal surrounding the reactor chamber acts as a temperature regulating body or by conventional heat exchangers.

Normally, a reaction mixture of a gaseous feed stream comprising a molecular oxygen containing gas, for example, air, a mixture of air and oxygen, mixtures of carbon dioxide and oxygen or mixtures of nitrogen or steam with air or oxygen, and a $C_4$ to $C_{10}$ hydrocarbon is charged to the reactor vessel. The gaseous feed stream generally will contain a molecular oxygen containing gas and from about 0.1 to about 2.5 mole percent, preferably from about 0.1 to about 1.5 mole percent, of a $C_4$ to $C_{10}$ hydrocarbon for optimum yield of maleic anhydride. Although higher concentrations of hydrocarbon may be employed, they are not recommended because explosive hazards may be encountered.

The $C_4$ to $C_{10}$ hydrocarbons which are suitable for use are selected from straight chain, branched chain, and cyclic alkanes or olefins. Suitable $C_4$ to $C_{10}$ alkanes include butane, pentane, isopentane, cyclopentane, hexane, cyclohexane, heptane, cycloheptane, octane, nonane, decane or mixtures thereof. Olefins which may be used to produce maleic anhydride are selected from mono- and di-olefins containing 4 to 10 carbon atoms. For example, desirable olefins include butene, butadiene, pentene, cyclopentene, isopentene, hexene, cyclohexene, heptene, cycloheptene, octene, nonene, decene or mixtures thereof.

Preferably, the molecular oxygen and $C_4$ to $C_{10}$ hydrocarbon are reacted in the presence of an oxidation catalyst of the invention. The flow rate of the gaseous feed stream through the pressure reactor may be varied within rather wide limits but a preferred flow rate is such that the gas hourly space velocity (GHSV) is from 700 to 5,000 reciprocal hours.

The temperature of reaction may be varied as necessary to achieve the desired conversion. The optimum temperature range for oxidizing the $C_4$ to $C_{10}$ hydrocarbons is usually from 500° F. to 1200° F. and preferably from 600° F. to 1000° F. It should be noted that the optimum oxidation temperatures for alkanes and olefins differ. For example, the optimum oxidation temperature range for $C_4$ to $C_{10}$ alkanes is from 750° F. to 1200° F., preferably from 800° F. to 1000° F., while the optimum oxidation temperature range for $C_4$ to $C_{10}$ olefins is from 500° F. to 900° F., preferably from 600° F. to 900° F.

Typically, the reaction pressure is from atmospheric pressure to 200 p.s.i.g., preferably from atmospheric pressure to 50 p.s.i.g. As previously stated, the reaction may be carried out in any reactor suitable for effecting vapor phase oxidation reactions, but preferably a vessel containing a fixed catalyst bed is employed.

The invention is further illustrated by the following examples which are illustrative of various aspects of the invention and are not intended as limiting the scope of the invention as defined by the appended claims.

EXAMPLE I

An oxidation catalyst of the invention is prepared by charging 28.0 grams of ammonium metavanadate and 100 ml of water to a 500 cc round-bottom flask equipped with a water-cooled condenser, heating mantle and magnetic stirrer. The resultant mixture is heated to a temperature of 130° F. and agitated with the magnetic stirrer for 3 minutes. Next, 20 ml of concentrated hydrochloric acid, 3.6 grams of stannous chloride, 20 ml of ethyl alcohol and 60.4 grams of 85 percent phosphoric acid are added to the above mixture. The non-homogeneous solution thus formed exhibits a green color. Finally, the solution is refluxed for 16 hours; however, a shorter reflux time period may be used, for example, ½ hour or more.

One-hundred-fifty milliliters of the dark green slurry produced by refluxing is mixed with 240 grams of H+ mordenite having a silica-to-alumina ratio of 10:1, and the resultant slurry is co-mulled with 20 grams of amorphous silica and 4 grams of methyl cellulose to achieve the proper consistency, using a Model No. 472 Lancaster Mixer, manufactured commercially by the Posey Iron Works, Inc., Lancaster, Pa. The mixer is operated at a speed of 36 RPM. The resulting slurry is extruded into cylindrical extrudates having an average length of ½ inch and an average diameter of 1/16 inch. The catalyst is activated by calcination at 932° F. in air for 3 hours and has a vanadium-phosphorus-tin atomic ratio of 0.43:1:0.034. The catalyst has a surface area of 308 $M^2/g$ and the vanadium has an average oxidation state of 4.37.

EXAMPLE II

Maleic anhydride is produced from n-butane by charging 25 ml of the catalyst of Example I to a reactor containing 82 ml of 4 to 6 mesh quartz granules. An additional 45 ml of 4 to 6 mesh quartz granules are added to the top of the catalyst as a preheat zone and n-butane distribution area. The reactor is a downflow tubular reactor having a length of 25 inches, an outside diameter of 1 inch, and an inside diameter of ¾ inch. In addition, the reactor is equipped with a ⅛ inch outside diameter, central-longitudinal thermowell. Air is charged to the reactor at the rate of 2.1 standard cubic feet (SCF)/hour and n-butane is charged to the reactor at a rate of 0.03 SCF/hour. The gas hourly space velocity (GHSV) is 2,400 hours$^{-1}$ and the catalyst bed temperature is 977° F. at atmospheric pressure. Analysis indicates that 16.6 percent of the n-butane is converted to maleic anhydride, with a selectivity of 125 weight percent and a yield of 23.1 weight percent to maleic anhydride production.

EXAMPLE III

The procedure of Example II is used to produce maleic anhydride with the following exceptions:

Pentane is substituted for the butane, the reaction temperature is 919° F. and the feed stream comprises air containing 1.47 mole percent pentane. Substantially the same conversion, selectivity and yield of maleic anhydride are obtained when pentane is substituted for butane.

EXAMPLES IV and V

Maleic anyhydride is produced from butene by charging 25 ml of the catalyst of Example I to a reactor containing 82 ml of 4 to 6 mesh quartz granules. An additional 45 ml of 4 to 6 mesh quartz granules are added to the top of the catalyst as a preheate zone and butene distribution area. The reactor is a downflow tubular reactor having a length of 25 inches, an outside diameter of 1 inch, and an inside diameter of ¾ inch. In addition, the reactor is equipped with a ⅛-inch outside diameter, central-longitudinal thermowell. A feed stream comprising air containing 1.5 mole percent of butene is charged to the reactor at the rate of 2.1 standard cubic feet (SCF)/hour. The reaction is conducted at atmospheric pressure. In addition, the temperature and gas hourly space velocity (GHSV) are varied in accordance with Table 1 below.

TABLE 1

| Ex | GHSV (Hours$^{-1}$) | T (°F.) | Weight Percent | | |
|----|---------------------|---------|----------------|-------------|-------|
|    |                     |         | Conversion     | Selectivity | Yield |
| IV | 2,500               | 766     | 78.9           | 66.8        | 52.5  |
| V  | 5,000               | 775     | 39.9           | 77.2        | 30.8  |

As can be seen from the foregoing examples, zeolitic catalysts are highly useful for converting $C_4$ to $C_{10}$ hydrocarbons to maleic anhydride. Although the invention is not be limited to any particular theory of operation, it is believed that the reason zeolites of low silica-to-alumina ratio (i.e., 6.0 or below) yield poor results with respect to the production of maleic anhydride is that the oxidation activity of the catalyst is adversely affected by a reaction (possibly a complexing) between the phosphorus component and the alumina in low silica-to-alumina zeolites, whether the alumina is present in an octahedral or tetrahedral form. Evidently, high silica-to-alumina ratios offer more protection to the alumina, preventing such reactions from occurring. In the following example, the poor results obtained with low silica-to-alumina ratio zeolites are illustrated.

EXAMPLE VI

The preparation in Example I was repeated except that a hydrothermally stabilized Y zeolite having a silica-to-alumina ratio of 5.4 was substituted for H+ mordenite. (The zeolite was prepared according to methods disclosed in U.S. Pat. Nos. 3,929,672 and 4,036,739.) The resulting catalyst contained vanadium in an average oxidation state of greater than +4.95 and, when tested for the oxidation of butene and butane, was found to exhibit essentially no activity for the desired conversion to maleic anhydride.

EXAMPLE VII

This example compares the effectiveness of a crystalline silica catalyst of the invention against an amorphous silica catalyst in the production of maleic anhydride.

CATALYST A

An oxidation catalyst containing crystalline silica was prepared in accordance with the invention by charging 2.8 grams of ammonium vanadate and 10 ml of water to a 100-cc round-bottomed flask equipped with a water-cooled condenser, heating mantle and magnetic stirrer. The above mixture was heated to a temperature of 130° F. with agitation for 3 minutes. Next, 6 grams of 85% phosphoric acid was added to the flask with continued heating and agitation for an additional 5 minutes. A mixture comprising 0.36 gram of stannous chloride dissolved in 2 ml of ethanol and 2 ml of hydrochloric acid was added to the flask and the resulting mixture was refluxed for 16 hours.

Silicalite (20 grams) and 15 ml of the above-described resulting mixture were mixed with 2 grams of siloid 65 (an amorphous silica) and 0.20 grams of methocel (methyl cellulose) to achieve the proper consistency. The resulting catalyst was dried at 230° F. for 2 hours and crushed to an average size of 20 to 30 mesh. The catalyst was activated at 932° F. in air for 3 hours. The catalyst contained vanadium having an average oxidation state of 4.66.

CATALYST B

An oxidation catalyst containing amorphous silica was prepared by charging 2.8 grams of ammonium vanadate and 10 ml of water to a 100-cc round-bottomed flask equipped with a water-cooled condenser, heating mantle and magnetic stirrer. The above mixture was heated to a temperature of 130° F. with agitation for 3 minutes. Next, 6 grams of 85% phosphoric acid was added to the flask with continued heating and agitation for an additional 5 minutes. A mixture comprising 0.36 gram of stannous chloride dissolved in 2 ml of ethanol and 2 ml of hydrochloric acid was added to the flask and the resulting mixture was refluxed for 16 hours.

Amorphous silica (20 grams) and 15 ml of the above-described resulting mixture were mixed with 2 grams of siloid 65 (an amorphous silica) and 0.20 grams of methocel (methyl cellulose). The resulting catalyst was dried at 230° F. for 2 hours and crushed to an average size of 20 to 30 mesh. The catalyst was activated at 932° F. in air for 3 hours. The catalyst contained vanadium having an average oxidation state of 4.65.

Test Procedure

Maleic anhydride was produced from n-butane by charging 25 ml of Catalyst A and Catalyst B, in separate runs, to a reactor containing 82 ml of 4 to 6 mesh quartz granules An additional 45 ml of 4 to 6 mesh quartz granules were added to the top of the catalyst as a pre-heat zone and n-butane distribution area. The reactor was a downflow tubular reactor having a length of 25 inches, an outside diameter of 1 inch, and an inside diameter of ¾ inch. In addition, the reactor was equipped with a ⅛-inch outside diameter, central-longitudinal thermowell. Air and n-butane were charged to the reactor at the rate of about 2.1 standard cubic feet (SCF)/hour, with the n-butane comprising about 1.5 mole percent of the total feed. The gas hourly space velocity (GHSV) was 2,400 hours$^{-1}$ and the catalyst bed temperature was as indicated in Table 2 below at atmospheric pressure. The results are summarized in Table 2.

TABLE 2

| Catalyst | Support | P/V[1] Ratio | AOS[2] | Temp.[3] °C. | Maleic Anhydride % Conversion | % Selectivity | % Yield |
|---|---|---|---|---|---|---|---|
| A | Crystalline Silica | 2.33 | 4.66 | 497 | 18 | 60 | 11 |
| B | Amorphous Silica | 2.30 | 4.65 | 461 | 23 | 39 | 9 |

[1] P/V Ratio = Phosphorus/Vanadium Ratio
[2] AOS = Average Oxidation State of Vanadium
[3] The temperature of the runs with Catalysts A and B was varied in an attempt to obtain a conversion rate as close to 20 percent as possible so that a comparison of the selectivities could be obtained. All other conditions were identical.

The foregoing data clearly reveal the superior selectivity of the catalyst of the invention (Catalyst A) for yielding maleic anhydride. Indeed, since it is well known that hydrocarbon oxidation catalysts tend to lose selectivity for producing maleic anhydride with increasing temperature, the fact that the catalyst of the invention was more than 50 percent more selective at a 36° C. higher operating temperature indicated that Catalyst A of the invention was far superior to Catalyst B.

Obviously, many modifications and variations of this invention, as hereinbefore set forth, may be made without departing from the spirit and scope thereof, and therefore only such limitations should be imposed as are indicated in the appended claims.

I claim:

1. A method for producing maleic anhydride which comprises contacting molecular oxygen and a $C_4$ to $C_{10}$ hydrocarbon under reaction conditions with an oxidation catalyst comprising vanadium and phosphorus components in combination with a microporous crystalline silica or a crystalline zeolite having a silica-to-alumina ratio of at least 6.0.

2. A method as defined in claim 1 wherein said catalyst further contains tin.

3. A method as defined in claim 1 wherein said catalyst contains a crystalline aluminosilicate zeolite having a silica-to-alumina ratio of at least 10.0.

4. A method for producing maleic anhydride as defined in claim 2 wherein the oxidation catalyst is prepared by:
   (A) contacting a vanadium compound and a phosphorus compound with an acidic aqueous medium and a divalent tin compound under reaction conditions which provide vanadium having an average valence of from +3.90 to +4.95 to form a catalyst precursor,
   (B) mixing the catalyst precursor with a zeolite having a silica-to-alumina ratio of at least 6.0, and
   (C) calcining the mixture from step (B).

5. A method as defined in claim 4 wherein said mixing in step (B) is with a crystalline alumino-silicate zeolite having a silica-to-alumina ratio of at least 8.0.

6. A method as defined in claim 4 wherein said mixing in step (B) is with a zeolite having a silica-to-alumina ratio of at least 10.0, and said medium in step (A) contains an alcohol.

7. The method defined in claim 1, wherein vanadium in said catalyst is present in an average oxidation state less than 5.

8. The method defined in claim 1 wherein vanadium in said catalyst is present in an average oxidation state between about 3.50 and 4.95.

9. The method defined in claim 1, wherein vanadium in said catalyst is present in an average oxidation state between about 4.10 and 4.70.

10. The method defined in claim 1, wherein said phosphorus and vanaium are present in said catalyst in an atom ratio of phosphorus to vanadium between 2.0 and 2.5, and said catalyst has a surface area at least 50 $M^2/gm$.

11. The method defined in claim 1, wherein said phosphorus and vanadium are present in said catalyst in an atom ratio of phosphorus to vanadium between about 2.2 and 2.4, and said catalyst has a surface area 150 to 400 $M^2/gm$.

12. The method defined in claim 1, wherein said catalyst is essentially free from alkali metals and alkaline earth metals.

13. The method defined in claim 1, wherein said catalyst contains a crystalline zeolite having a silica-to-alumina ratio at least 8.0.

14. The method defined in claim 1, wherein said catalyst contains a zeolite of the Y crystal structure.

15. The method defined in claim 1, wherein said catalyst contains a type ZSM-5 zeolite.

16. The method defined in claim 1, wherein said catalyst contains a microporous crystalline silica, said phosphorus and vanadium are present in said catalyst in an atom ratio of phosphorus to vanadium between 2.0 and 2.5, and said catalyst has a surface area at least 50 $M^2/gm$.

17. The method defined in claim 16, wherein the atom ratio of phosphorus to vanadium is between about 2.2 and 2.4, and said surface area is 150 to 400 $M^2/gm$.

18. A method for producing maleic anhydride which comprises contacting molecular oxygen and a $C_4$ to $C_{10}$ hydrocarbon under reaction conditions with an oxidation catalyst comprising vanadium and phosphorus components in combination with a microporous crystalline silica or a crystalline zeolite having a silica-to-alumina ratio at least 6.0, said vanadium being present in an oxidation state less than 5.0.

19. The method defined in claim 18, wherein vanadium in said catalyst is present in an average oxidation state between about 3.50 and 4.95.

20. The method defined in claim 18, wherein vanadium in said catalyst is present in an average oxidation state between about 4.10 and 4.70.

21. The method defined in claim 18, wherein said catalyst contains a crystalline zeolite having a silica-to-alumina ratio at least 8.0.

22. The method defined in claim 21, wherein said phosphorus and vanadium are present in said catalyst in an atom ratio of phosphorus to vanadium between about 2.0 and 2.5, and said catalyst has a surface area at least about 50 $M^2/gm$.

23. The method defined in claim 18, wherein said phosphorus and vanadium are present in said catalyst in an atom ratio of phosphorus to vanadium between about 2.2 and 2.4, and said catalyst has a surface area 150 to 400 $M^2/gm$.

24. The method defined in claim 23, wherein said catalyst is essentially free from alkali metals and alkaline earth metals.

25. The method defined in claim 18, wherein said catalyst contains a crystalline zeolite having a silica-to-alumina ratio at least 10.0.

26. The method defined in claim 25, wherein said catalyst further contains tin.

27. A method for producing maleic anhydride which comprises contacting molecular oxygen and a $C_4$ to $C_{10}$ hydrocarbon under reaction conditions with an oxidation catalyst comprising vanadium and phosphorus components in combination with a microporous crystalline silica or a crystalline zeolite having a silica-to-alumina ratio at least 6.0, said vanadium being present in an oxidation state less than 5.0, said phosphorus and vanadium being present in an atom ratio of phosphorus to vanadium between 2.0 and 2.5, and said catalyst having a surface arca at least 50 $M^2/gm$.

28. The method defined in claim 27, wherein vanadium in said catalyst is present in an average oxidation state between about 3.50 and 4.95.

29. The method defined in claim 27, wherein vanadium in said catalyst is present in an average oxidation state between about 4.10 and 4.70.

30. The method defined in claim 28, wherein said phosphorus and vanadium are present in said catalyst in an atom ratio of phosphorus to vanadium between about 2.2 and 2.4, and said catalyst has a surface area 150 to 400 $M^2/gm$.

31. The method defined in claim 30, wherein said catalyst is essentially free from alkali metals and alkaline earth metals.

32. The method defined in claim 31, wherein said catalyst contains a crystalline zeolite having a silica-to-alumina ratio at least 8.0.

33. The method defined in claim 28, wherein said catalyst contains a crystalline zeolite having a silica-to-alumina ratio at least 10.0.

34. The method defined in claim 32, wherein said catalyst further contains tin.

* * * * *